(12) United States Patent
Woelk et al.

(10) Patent No.: US 7,141,488 B2
(45) Date of Patent: Nov. 28, 2006

(54) METHOD OF DEPOSITING GERMANIUM-CONTAINING FILMS

(75) Inventors: Egbert Woelk, North Andover, MA (US); Deodatta Vinayak Shenai-Khatkhate, Danvers, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 188 days.

(21) Appl. No.: 10/816,356

(22) Filed: Apr. 2, 2004

(65) Prior Publication Data

US 2004/0197945 A1   Oct. 7, 2004

Related U.S. Application Data

(60) Provisional application No. 60/513,475, filed on Oct. 22, 2003, provisional application No. 60/513,476, filed on Oct. 22, 2003, provisional application No. 60/460,791, filed on Apr. 5, 2003.

(51) Int. Cl.
*H01L 21/205* (2006.01)
(52) U.S. Cl. .................................. 438/478; 427/255.28
(58) Field of Classification Search ................. 438/478
See application file for complete search history.

(56) References Cited

U.S. PATENT DOCUMENTS

| | | | |
|---|---|---|---|
| 2,444,270 A | 6/1948 | Rochow | |
| 3,446,824 A | 5/1969 | Moedritzer | |
| 3,470,220 A | 9/1969 | Moedritzer et al. | |
| 3,935,040 A | 1/1976 | Mason | |
| 3,985,590 A | 10/1976 | Mason | |
| 4,506,815 A | 3/1985 | Melas et al. | |
| 4,720,561 A | 1/1988 | Bradley et al. | |
| 4,812,586 A | 3/1989 | Mullin et al. | |
| 5,120,394 A | 6/1992 | Mukai | |
| 5,316,958 A | 5/1994 | Meyerson | |
| 5,489,550 A | 2/1996 | Moslehi | |
| 5,502,227 A | 3/1996 | Kanjolia et al. | |
| 5,755,885 A | 5/1998 | Mikoshiba et al. | |
| 6,099,903 A | 8/2000 | Kaloyeros et al. | |
| 6,214,729 B1 | 4/2001 | Uhlenbrock et al. | |
| 6,238,734 B1 | 5/2001 | Senzaki et al. | |
| 6,306,217 B1 | 10/2001 | Uhlenbrock et al. | |
| 6,391,803 B1 | 5/2002 | Kim et al. | |
| 6,444,038 B1 | 9/2002 | Rangarajan et al. | |
| 6,444,041 B1 | 9/2002 | Vaartstra | |
| 6,444,818 B1 | 9/2002 | Uhlenbrock et al. | |
| 6,492,711 B1 | 12/2002 | Takagi et al. | |
| 6,509,587 B1 | 1/2003 | Sugiyama et al. | |
| 6,514,886 B1 | 2/2003 | U'Ren | |
| 6,759,697 B1 * | 7/2004 | Toyoda et al. | 257/197 |
| 2003/0045075 A1 * | 3/2003 | Joo et al. | 438/507 |
| 2003/0082300 A1 | 5/2003 | Todd et al. | |
| 2003/0111013 A1 | 6/2003 | Oosterlaken et al. | |
| 2003/0230233 A1 | 12/2003 | Fitzgerald et al. | |
| 2004/0259333 A1 | 12/2004 | Tomasini et al. | |

FOREIGN PATENT DOCUMENTS

| | | |
|---|---|---|
| EP | 0 368 651 B1 | 9/1994 |
| EP | 1 160 355 A2 | 12/2001 |
| GB | 626398 | 7/1949 |
| GB | 1 386 900 | 3/1975 |
| WO | WO 2004/011473 A1 | 2/2004 |

OTHER PUBLICATIONS

Dittmar et al., Cyclopentadienyl Germanes as Novel Precursors for the CVD of Thin Germanium Films, Chem. Vap. Deposition 2001, 7, No. 5, pp. 193-195.

Harrison et al., "Predeposition Chemistry Underlying the Formation of Germanium Films by CVD of Tetravinylgermane", Chem. Mater. 1994, 6, pp. 1620-1626.

Hoffman et al., "Plasma-enhanced chemical vapor deposition of silicon, germanium, and tin nitride thin films from metalorganic precursors", J. Vac. Sci. Technol. A. 13(3), May/Jun. 1995, pp. 820-825.

O. Johnson, "The Germanes and Their Organo Derivatives" Chem. Rev. 1951, 48, 259, pp. 259, pp. 259-297.

Kidd et al., "Germanium-73 Nuclear Magnetic Resonance Spectra of Germanium Tetrahalides", Journal of American Chemical Society, 95:1, Jan. 10, 1973, pp. 88-90.

H. Ohshima, "Organo-germanium adsorption on a silicon surface by excimer light irradiation", Applied Surface Science 107(1996) pp. 85-89.

Bottei et al., "Organogermanium Chemistry", Chem. Rev. (1951), 48, 259, pp. 403-442.

Sulkes et al., "Molecular beam study of possible CVD intermediates from Group-14 organometallic precursors", Chemical Physics Letters 318 (2000) pp. 448-453.

D. Smith, Structural Properties of heteroepitaxial germanium-carbon alloys grown on Si(100); Philosophical Magazine A, 2001, vol. 81, No. 6, pp. 1613-1624.

Todd et al., "Influence on Precursor Chemistry on Synthesis of Silicon-Carbon Germanium Alloys", Mat. Res. Soc. Symp. Proc. vol. 377, 1995, pp. 529-534.

Dillon et al.; "Comparison of Trichlorosilane and Trichlorogermane Decomposition on Silicon Surfaces Using FTIR Spectroscopy"; Mat. Res. Soc. Symp. Proc. vol. 282; 1993; pp. 405-411.

Dillon et al.; "Adsorption and Decomposition of Diethylgermane on porous silicon surfaces"; Surface Science Letters 286 (1993); pp. L535-L541.

(Continued)

*Primary Examiner*—Stephen W. Smoot
(74) *Attorney, Agent, or Firm*—S. Matthew Cairns

(57) ABSTRACT

Germanium compounds suitable for use as vapor phase deposition precursors for germanium films are provided. Methods of depositing films containing germanium using such compounds are also provided. Such germanium films are particularly useful in the manufacture of electronic devices.

15 Claims, No Drawings

OTHER PUBLICATIONS

Todd et al.; Chemical Synthesis of Metastable Germanium-Carbon Alloys Grown Heteroepitaxially on (100) Si; Chem. Mater. 1996, 8, pp. 2491-2498.

Coon et al.; "Germanium Deposition on Silicon: Surface Chemistry of $(CH_3CH_2)_2GeH_2$ and $GeCl_4$"; Mat. Res. Soc. Symp. Proc. vol. 282; 1993; pp. 413-419.

Kouvetakis et al.; "Novel Chemical Routes to Silicon-Germanium-Carbon Materials"; Appl. Phys. Lett. 65 (23); Dec. 5, 1994; pp. 2960-2962.

Dillon et al.; "Adsorption and Decomposition of Trichlorosilane and Trichlorogermane on Porous Silicon and Si(100)2×1 Surfaces"; J. Vac. Sci. Technol. A 13(1); Jan./Feb. 1995; pp. 1-10.

* cited by examiner

METHOD OF DEPOSITING GERMANIUM-CONTAINING FILMS

This application claims the benefit of provisional application Ser. No. 60/460,791, filed on Apr. 5, 2003, and provisional application Ser. No. 60/513,475, filed on Oct. 22, 2003, and provisional application Ser. No. 60/513,476, filed on Oct. 22, 2003.

BACKGROUND OF THE INVENTION

The present invention relates generally to the field of germanium compounds. In particular, the present invention relates to the certain germanium compounds suitable for use in vapor deposition processes.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), chemical beam epitaxy ("CBE") and atomic layer deposition ("ALD"). Chemical vapor deposition processes, such as metalorganic chemical vapor deposition ("MOCVD"), deposit a metal layer by decomposing organometallic precursor compounds at elevated temperatures, i.e., above room temperature, either atmospheric pressure or at reduced pressures. A wide variety of metals may be deposited using such CVD or MOCVD processes.

For semiconductor and electronic device applications, these organometallic precursor compounds must be highly pure and be substantially free of detectable levels of both metallic impurities, such as silicon and zinc, as well as oxygenated impurities. Oxygenated impurities are typically present from the solvents used to prepare such organometallic compounds, and are also present from other adventitious sources of moisture or oxygen.

For certain applications where high speed and frequency response of an electronic device is desired, silicon-only devices, e.g. silicon bipolar transistors, perform marginally and the introduction of germanium is necessary to obtain the desired functionality. In a heterojunction bipolar transistor ("HBT"), a thin silicon-germanium layer is grown as the base of a bipolar transistor on a silicon wafer. The silicon-germanium HBT has significant advantages in speed, frequency response, and gain when compared to a conventional silicon bipolar transistor. The speed and frequency response of a silicon-germanium HBT are comparable to more expensive gallium-arsenide HBTs.

The higher gain, speeds, and frequency response of silicon-germanium HBTs have been achieved as a result of certain advantages of silicon-germanium not available with pure silicon, for example, narrower band gap and reduced resistivity. Silicon-germanium may be epitaxially grown on a silicon substrate using conventional silicon processing and tools. This technique allows one to engineer device properties such as the energy band structure and carrier mobility. For example, it is known in the art that grading the concentration of germanium in the silicon-germanium base builds into the HBT device an electric field or potential gradient, which accelerates the carriers across the base, thereby increasing the speed of the HBT device compared to a silicon-only device. A common method for fabricating silicon and silicon-germanium devices is by CVD. A reduced pressure chemical vapor deposition technique ("RPCVD") used to fabricate the HBT device allows for a controlled grading of germanium concentration across the base layer as well as precise control over the doping profile.

Germane ($GeH_4$) is the conventional precursor for germanium deposition. Germane is a gas under standard conditions and is difficult to handle. As germane is toxic, processes employing germane require extensive safety procedures and equipment. Germane typically requires film growth temperatures of approximately 500° C. for thermal CVD applications. Such decomposition temperatures are not always suitable, such as in applications where there is a need for lower temperatures, e.g. 200° C. Other CVD applications require higher growth temperatures, e.g. 700–1100° C., which cause germane to break up prematurely which, in turn, leads to the formation of particles and a reduction in metal film growth rates. A further problem with germanium precursors arises in silicon-germanium deposition when a relatively stable silicon precursor and a relatively unstable germanium precursor (germane) are used to deposit a silicon-germanium film, the differences in precursor stability makes control of the silicon-germanium composition difficult.

U.S. patent application Ser. No. 2003/0111013 (Oosterlaken et al.) discloses an apparatus for the deposition of silicon germanium layers. This application discloses certain source compounds for the vapor deposition of germanium, such as mono-, di- tri- and tetra-chlorogermanes. Such compounds may not be suitable for all germanium vapor deposition applications as their decomposition temperatures may be too low. For example, monochlorogermane is known to decompose at temperatures as low as 25° C.

There remains a need for germanium precursors that offer an optimized deposition of germanium-containing films at various growth temperatures. Such growth temperatures determine the properties of the germanium-containing film. A limitation in growth temperature limits the full exploitation of the capabilities of a germanium-containing film. There remains a need for germanium precursors for CVD that are safer to handle.

SUMMARY OF THE INVENTION

The present inventors have surprisingly found that the above limitations on the deposition of germanium by CVD can be remedied. The present invention provides a method of depositing a film containing germanium on a substrate including the steps of: a) conveying two or more germanium compounds in a gaseous phase to a deposition chamber containing the substrate, wherein a first germanium compound is a halogermanium compound of the formula $X^1_{4-a}GeR_a$, wherein a = 0–3, each $X^1$ is independently a halogen, and each R is independently chosen from H, alkyl, alkenyl, alkynyl, aryl, and $NR^4R^6$, wherein each $R^4$ and $R^6$ are independently chosen from H, alkyl, alkenyl, alkynyl and aryl, and wherein a second germanium compound has the formula

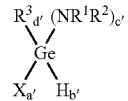

wherein each $R^1$ and $R^2$ are independently chosen from H, alkyl, alkenyl, alkynyl and aryl; each $R^3$ is independently chosen from alkyl, alkenyl, alkynyl and aryl; X is halogen; a'=0–4; b'=0–4; c'=0–3; d'=0–4 and a'+b'+c'+d'=4; provided that a'+b'≦3 when $X^1$=Cl, R=H, and X=Cl; b) decomposing the two or more germanium compounds in the deposition chamber; and c) depositing the film comprising germanium on the substrate.

Further, the present invention provides a method of manufacturing an electronic device including the step of depositing a film containing germanium on a substrate wherein the film including the steps of: a) conveying two or more germanium compounds in a gaseous phase to a deposition chamber containing the substrate, wherein a first germanium compound is a halogermanium compound of the formula $X^1_{4-a}GeR_a$, wherein a=0–3, each $X^1$ is independently a halogen, and each R is independently chosen from H, alkyl, alkenyl, alkynyl, aryl, and $NR^4R^6$, wherein each $R^4$ and $R^6$ are independently chosen from H, alkyl, alkenyl, alkynyl and aryl, and wherein a second germanium compound has the formula

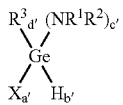

wherein each $R^1$ and $R^2$ are independently chosen from H, alkyl, alkenyl, alkynyl and aryl; each $R^3$ is independently chosen from alkyl, alkenyl, alkynyl and aryl; X is halogen; a'=0–4; b'=0–4; c'=0–3; d'=0–4 and a'+b'+c'+d'=4; provided that a'+b'≦3 when $X^1$=Cl, R=H, and X=Cl; b) decomposing the two or more germanium compounds in the deposition chamber; and c) depositing the film comprising germanium on the substrate.

The present invention also provides a composition including two or more germanium compounds; wherein a first germanium compound is a halogermanium compound of the formula $X^1_{4-a}GeR_a$, wherein a=0–3, each $X^1$ is independently a halogen, and each R is independently chosen from H, alkyl, alkenyl, alkynyl, aryl, and $NR^4R^6$, wherein each $R^4$ and $R^6$ are independently chosen from H, alkyl, alkenyl, alkynyl and aryl, and wherein a second germanium compound has the formula

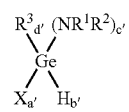

wherein each $R^1$ and $R^2$ are independently chosen from H, alkyl, alkenyl, alkynyl and aryl; each $R^3$ is independently chosen from alkyl, alkenyl, alkynyl and aryl; X is halogen; a'=0–4; b'=0–4; c'=0–3; d'=0–4 and a'+b'+c'+d'=4; provided that a'+b'≦3 when $X^1$=Cl, R=H, and X=Cl.

Still further, the present invention provides a vapor delivery device suitable for feeding a fluid stream saturated with a germanium compound suitable for depositing a film containing germanium to a chemical vapor deposition system including a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing two or more germanium compounds; the inlet opening being in fluid communication with the chamber and the chamber being in fluid communication with the outlet opening. In one embodiment, the two or more germanium compounds include a first halogermanium compound of the formula $X^1_{4-a}GeRa$, wherein a=0–3, each $X^1$ is independently a halogen, and each R is independently chosen from H, alkyl, alkenyl, alkynyl, aryl, and $NR^4R^6$, wherein each $R^4$ and $R^6$ are independently chosen from H, alkyl, alkenyl, alkynyl and aryl, and a second germanium compound of the formula

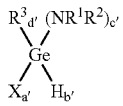

wherein each $R^1$ and $R^2$ are independently chosen from H, alkyl, alkenyl, alkynyl and aryl; each $R^3$ is independently chosen from alkyl, alkenyl, alkynyl and aryl; X is halogen; a'=0–4; b'=0–4; c'=0–3; d'=0–4 and a'+b'+c'+d'=4; provided that a'+b'≦3 when $X^1$=Cl,R=H, and X=Cl.

Another embodiment of the present invention is an apparatus for vapor deposition of metal films including one or more devices for feeding a fluid stream including two or more germanium compounds, such as those described above.

DETAILED DESCRIPTION OF THE INVENTION

As used throughout this specification, the following abbreviations shall have the following meanings, unless the context clearly indicates otherwise: ° C.=degrees centigrade; mol=moles; g=gram; ca.=approximately; and μm=micron=micrometer.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. The term "SiGe" refers to silicon-germanium. As used herein, "CVD" is intended to include all forms of chemical vapor deposition such as MOCVD, MOVPE, OMVPE, OMCVD and RPCVD. The articles "a" and "an" refer to the singular and the plural.

Unless otherwise noted, all amounts are percent by weight and all ratios are molar ratios. All numerical ranges are inclusive and combinable in any order except where it is clear that such numerical ranges are constrained to add up to 100%.

The present invention provides a method of depositing a film containing germanium on a substrate including the steps of: a) conveying two or more germanium compounds in a gaseous phase to a deposition chamber containing the substrate, wherein a first germanium compound is a halogermanium compound of the formula $X^1_{4-a}GeR_a$, wherein a=0–3, each $X^1$ is independently a halogen, and each R is independently chosen from H, alkyl, alkenyl, alkynyl, aryl, and $NR^4R^6$, wherein each $R^4$ and $R^6$ are independently chosen from H, alkyl, alkenyl, alkynyl and aryl, and wherein a second germanium compound has the formula

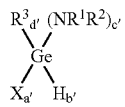

wherein each $R^1$ and $R^2$ are independently chosen from H, alkyl, alkenyl, alkynyl and aryl; each $R^3$ is independently chosen from alkyl, alkenyl, alkynyl and aryl; X is halogen; a'=0–4; b'=0–4; c'=0–3; d'=0–4 and a'+b'+c'+d'=4; provided that a'+b'≦3 when $X^1$=Cl, R=H, and X =Cl; b) decomposing the two or more germanium compounds in the deposition chamber; and c) depositing the film comprising germanium on the substrate. In one embodiment, the second germanium compound is an alkyl germane. Exemplary alkyl germanes include, without limitation, those compounds having the above formula where a'=c'=0, d'=2–3, and b'=1–2. In a further embodiment, the alkyl germanium compound is a heteroleptic alkyl germanium compound. By "herteroleptic alkyl germanium compound" is meant a germanium compound having mixed alkyl groups, i.e., a germanium compound having two or more alkyl groups where at least two of the alkyl groups are different. Exemplary heteroleptic alkyl germanium compounds include those of the formula $R^5_z GeH_y$; wherein each $R^5$ is independently chosen from alkyl, alkenyl, alkynyl and aryl; z=2–3; and y=1–2.

In another embodiment, at least two halogermanium compounds are used. As used herein, the term "halogermanium compound" refers to any germanium compound having one or more halogens bonded directly to the germanium. The present halogermanium compounds may have a wide variety of other groups bonded to the germanium, provided that at least one halogen is bonded to the germanium. It will be clear to those skilled in the art that three, four or more different germanium compounds, particularly halogermanium compounds, may be advantageously used in the present invention.

A wide variety of halogermanium compounds may be used, such as, but not limited to, tetrahalogermanes and halogermanium compounds of the formula $X^1_{4-a}GeR_a$, wherein each R is independently chosen from H, alkyl, alkenyl, alkynyl, aryl and $NR^1R^2$; $R^1$ and $R^2$ are independently chosen from H, alkyl, alkenyl, alkynyl and aryl; each $X^1$ is independently halogen; and a=0–3. The tetrahalogermanes have the formula $GeX^1_4$, wherein each X is independently a halogen. When two or more halogens are present in the halogermanium compounds, such halogens may be the same or different.

A wide variety of alkyl, alkenyl and alkynyl groups may be used for R, $R^1$ and $R^2$. Suitable alkyl groups include, without limitation, $(C_1-C_{12})$alkyl, typically $(C_1-C_6)$alkyl and more typically $(C_1-C_4)$alkyl. Exemplary alkyl groups include, but are not limited to, methyl, ethyl, n-propyl, iso-propyl, n-butyl, iso-butyl, sec-butyl, tert-butyl, pentyl, cyclopentyl, hexyl, and cyclohexyl. More typically, suitable alkyl groups include ethyl, iso-propyl, and tert-butyl. Suitable alkenyl groups include, without limitation, $(C_2-C_{12})$alkenyl, typically $(C_2-C_6)$alkenyl and more typically $(C_2-C_4)$alkenyl. Exemplary alkenyl groups include vinyl, allyl, methallyl and crotyl. Typical alkynyl groups include, without limitation, $(C_2-C_{12})$alkynyl, typically $(C_2-C_6)$alkynyl and more typically $(C_2-C_4)$alkynyl. Suitable aryl groups are $(C_6-C_{10})$aryl, including, but not limited to, phenyl, tolyl, xylyl, benzyl and phenethyl. When two or more alkyl, alkenyl or alkynyl groups are present, such groups may be the same or different.

Typical amino ($NR^1R^2$) groups for R include, but are not limited to, dimethylamino, diethylamino, di-iso-propylamino, ethylmethylamino, iso-propylamino, and tert-butylamino. However, other suitable amino groups may be used.

Any of the above alkyl, alkenyl, alkynyl or aryl groups of R, $R^1$ and $R^2$ may optionally be substituted with one or more amino ($NR^4R^6$) groups, wherein $R^4$ and $R^6$ are independently chosen from H, alkyl, alkenyl, alkynyl and aryl. By "substituted" it is meant that one or more hydrogens on the alkyl, alkenyl, alkynyl or aryl group is replaced with one or more $NR^4R^6$ groups. Exemplary alkyl substituted with $NR^4R^6$ groups include, without limitation, dimethylaminomethyl (($CH_3)_2N-CH_2-$), dimethylamino-ethyl (($CH_3)_2N-C_2H_4-$), diethylamino-ethyl (($C_2H_5)_2N-C_2H_4-$), dimethylamino-propyl (($CH_3)_2N-C_3H_6-$), and diethylamino-propyl (($C_2H_5)_2N-C_3H_6-$).

Exemplary halogermanium compounds include, without limitation: the tetrahalogermanium compounds such as tetrachloro germane, tetrafluoro germane, tetrabromo germane, tetraiodo germane, chloro tribromo germane, dichloro dibromo germane, trichloro bromo germane, trichloro iodo germane, dichloro diiodo germane, trichloro iodo germane, tribromo iodo germane, dibromo diiodo germane, bromo triiodo germane, dichloro bromo iodo germane, chloro dibromo iodo germane, chloro bromo diiodo germane, trichloro fluoro germane, dichloro difluoro germane, chloro trifluoro germane, tribromo fluoro germane, dibromo difluoro germane, bromo trifluoro germane, iodo trifluoro germane, diiodo difluoro germane, triiodo fluoro germane, chloro bromo iodo fluoro germane, dichloro bromo fluoro germane, chloro dibromo fluoro germane, dibromo iodo fluoro germane, bromo diiodo fluoro germane, dichloro iodo fluoro germane and chloro diiodo fluoro germane; and iso-propyl (dimethylamino) germanium dichloride; methyl (dimethylamino) germanium dichloride; methyl (dimethylamino) germanium dibromide; dichloro (diethylamino) germane; dichloro ethyl (diethylamino) germane; dichloro tert-butyl (diethylamino) germane; dichloro bis(dimethylamino) germane; and chloro ethyl (dimethylaminopropyl) (dimethylamino) germane; dichloro tert-butyl (dimethylamino) germane; chloro di-iso-propyl (dimethylamino) germane; trimethyl germanium chloride; methyl germanium trichloride; trimethyl germanium fluoride; trimethyl germanium bromide; tris(trifluoromethyl) germanium iodide; methyl germanium trifluoride; dimethyl germanium difluoride; dichloro methyl germane; dimethyl germanium dichloride; trimethyl germanium iodide; vinyl germanium trichloride; ethyl germanium trichloride; chloro tert-butyl dimethyl germane; allyl germanium trichloride; iso-butyl germanium trichloride; tert-butyl germanium trichloride; diethyl germanium dichloride; trimethyl germanium chloride; n-butyl germanium trichloride; trimethyl germanium bromide; di-n-butyl germanium dichloride; phenyl germanium dichloride; tri-n-butyl germanium bromide; tri-n-butyl germanium chloride; and benzyl germanium trichloride.

Exemplary germanium compounds, suitable for use as the second germanium compound, include without limitation: germane, alkyl germanes such as tetramethyl germane, tetraethyl germane, tetra-n-propyl germane, methyl germane, dimethyl germane, trimethyl germane, ethyl germane, diethyl germane, trimethyl germane, dimethyl diethyl germane, tert-butyl methyl germane, tert-butyl dimethyl germane, tert-butyl triethyl germane, tert-butyl ethyl germane, tert-butyl diethyl germane, tert-butyl trimethyl germane, tert-butyl iso-propyl germane, methyl tert-butyl iso-propyl germane, iso-propyl germane, di-iso-propyl germane, di-iso-propyl dimethyl germane, tri-iso-propyl germane, tri-iso-propyl methyl germane, tert-butyl germane, iso-butyl germane, n-propyl germane and di-iso-propyl diethyl germane; amino germanes such as (dimethylamino) germane, bis-(dimethylamino) germane, methyl (dimethylamino) germane, ethyl (dimethylamino) germane, diethyl (diethylamino) germane, tert-butyl (dimethylamino)germane, tert-butyl bis(dimethylamino) germane, ethyl tert-butyl bis (dimethylamino) germane, iso-propyl (dimethylamino) germane, iso-propyl (diethylamino) germane, di-iso-propyl bis(dimethylamino) germane, n-propyl (dimethylamino) germane, and n-propyl (diethylamino) germane; and halogermanium compounds such as tert-butyl dimethyl germanium chloride, tert-butyl dimethyl germanium bromide, tert-butyl diethyl germanium chloride, tert-butyl diethyl germanium iodide, dimethyl germanium dichloride, trimethyl germanium chloride, trimethyl germanium bromide, tert-butyl germanium trichloride, iso-butyl germanium trichloride, iso-propyl germanium chloride, iso-propyl germanium trichloride, di-iso-propyl germanium dibromide, iso-propyl dimethyl germanium chloride, iso-propyl methyl germanium dichloride, and iso-propyl dimethyl germanium bromide.

The two or more germanium compounds may be present in a wide range of ratios, such as in a mole ratio of 1:99 to 99:1. Typically, the two germanium compounds, such as two halogermanium compounds, are present in a mole ratio of 25:75 to 75:25, and more typically from 35:65 to 65:35. In one embodiment, at least two halogermanium compounds are present. In another embodiment, at least one halogermanium compound, particularly a tetrahalogermanium compound, and germane are used.

In general, the two or more germanium compounds used in the present invention are selected such that the mixture of the germanium compounds provides a stable concentration of germanium source in the vapor phase. This is achieved by using a combination of two or more germanium compounds, wherein a first germanium compound is a halogermanium compound. Any germanium compound may be used as the second germanium compound, however a halogermanium compound is preferred. In one embodiment, the two or more germanium compounds become very difficult to separate once mixed. The more difficult it is to separate the mixed germanium compounds, the more stable the concentration of the germanium source in the vapor phase. An advantage of the present invention is that the properties of a germanium source can be tailored to desired reaction conditions. For example, a germanium source having a certain vapor pressure can be prepared by combining two or more germanium compounds that individually do not have the desired vapor pressure. In this illustration, a germanium compound having a vapor pressure higher than the desired vapor pressure and a germanium compound having a vapor pressure lower than that desired can be mixed to provide a germanium source having the desired vapor pressure. As used herein, "germanium source" refers to a vapor phase germanium compound or compounds that are provided to a reactor for deposition of a film containing germanium.

A further advantage of the present invention is that the presence of halogens in the germanium compounds leads to the formation of hydrogen halide acids in the vapor phase, such as gaseous hydrogen chloride and hydrogen fluoride. Such gaseous hydrogen halide acids are effective in cleaning the reactor during use. For example, the gaseous hydrogen halide acids may remove solid particles deposited along the reactor walls, thus minimizing reactor maintenance.

The present halogermanium compounds may be prepared by a variety of procedures. Typically, such compounds are prepared starting from a compound of the formula $GeY_4$ where Y is a reactive group such as a halogen, an acetate or a $(C_1–C_4)$alkoxy, with halogens being most typical. As used herein, a reactive group is any group attached to the germanium that is displaced or exchanged in a subsequent reaction.

Dialkylamino-substituted halogermanium compounds may be prepared by the reaction of a dialkylamine in liquid or gaseous forms with a germanium compound having one or more reactive groups and more typically is prepared by the reaction of a dialkylamino lithium reagent with such germanium compound having one or more reactive groups. Such reactions are typically performed in a hydrocarbon solvent, such as but not limited to hexane, heptane, octane, nonane, decane, dodecane, toluene, and xylene. Preferably, such solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen. For example, germanium tetrachloride may be reacted with a sufficient amount of dialkylamino lithium reagent to provide a desired dialkylamino germanium halide compound. This reaction is illustrated in Equation 1.

$$2\ LiNMe_2 + GeCl_4 \rightarrow (NMe_2)_2GeCl_2 + 2LiCl \tag{1}$$

Alkyl, alkenyl, alkynyl and aryl substituted halogermanium compounds may be prepared using Grignard or organolithium reactions. Such reactions are well known to those skilled in the art. In a typical Grignard reaction, a compound having one or more reactive groups is reacted with a Grignard reagent, such as methyl magnesium bromide or allyl magnesium bromide in an ethereal solvent. Typical ethereal solvents include, without limitation, diethyl ether, di-isopropyl ether, n-butyl ether, iso-pentyl ether, dihexyl ether, diheptyl ether, tetrahydrofuran, dioxane, monoglyme, diglyme, diethylene glycol dibutyl ether, diethylene glycol monobutyl ether, ethylene glycol dibutyl ether, ethylene glycol monohexyl ether, ethylene glycol monobenzyl ether, tetraethylene glycol dimethyl ether, triethylene glycol dimethyl ether, butyl phenyl ether, and dicyclohexyl ether. Such solvents are typically deoxygenated prior to use as described above. This reaction is illustrated in Equation 2.

$$(NMe_2)_2GeCl_2 + AllylMgBr \rightarrow (NMe_2)_2Ge(Allyl)Cl + MgBrCl \tag{2}$$

In a typical organolithium reaction, a compound having one or more reactive groups is reacted with an organolithium reagent, such as methyl lithium, tert-butyl lithium, n-butyl lithium and phenyl lithium in a hydrocarbon solvent. Suitable solvents are those described above for the dialkylamino lithium reaction. Equation 3 illustrates the reaction of bis (dimethylamino) germanium dichloride with iso-propyl lithium.

$$(NMe_2)_2GeCl_2 + i\text{-}PrLi \rightarrow (NMe_2)_2Ge(i\text{-}Pr)Cl + LiCl \tag{3}$$

In another embodiment, a germanium compound having two or more reactive groups may be reacted with two different lithium reagents in one pot. Such different lithium reagents may be two different organolithium reagents, two different dialkylamino lithium reagents or a mixture of an organolithium reagent and a dialkylamino lithium reagent. In such reaction, the different lithium reagents may be added to the reaction simultaneously or in a stepwise manner. Equation 4 illustrates this reaction sequence for the reaction of germanium tetrachloride with tert-butyl lithium and dimethylamino lithium.

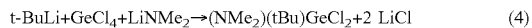

$$t\text{-BuLi} + GeCl_4 + LiNMe_2 \rightarrow (NMe_2)(tBu)GeCl_2 + 2\ LiCl \quad (4)$$

In a further embodiment, the alkyl-, alkenyl-, alkynyl- and aryl-substituted germanes may be prepared by a transalkylation reaction using the appropriately substituted aluminum compound. For example, methyl-substituted germanes may be prepared by the reaction of an appropriate amount of trimethylaluminum with an appropriate amount of germanium tetrachloride in the presence of a tertiary amine. Such amounts are well within the ability of those skilled in the art. Equation 5 illustrates this reaction sequence for the reaction of germanium tetrachloride with trimethylaluminum.

$$2GeCl_4 + AlMe_3 \rightarrow 2MeGeCl_3 + MeAlCl_2 \quad (5)$$

Such transalkylation reactions using alkyl aluminum compounds are preferably performed in the presence of a tertiary amine. Any tertiary amine may suitably be used. Exemplary tertiary amines include, but are not limited to, those having the general formula NR'R"R''', wherein R", R" and R''' are independently selected from $(C_1-C_6)$alkyl, $di(C_1-C_6)$alkylamino-substituted $(C_1-C_6)$alkyl, and phenyl and wherein R' and R" may be taken together along with the nitrogen to which they are attached to form a 5–7 membered heterocyclic ring. Such heterocyclic ring may be aromatic or non-aromatic. Particularly suitable tertiary amines include, but are not limited to, trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperidine, N-iso-propylpiperidine, N,N'-dimethylpiperazine, N,N'-diethylpiperazine, N,N'-dipropylpiperazine, N,N,N', N'-tetramethyl-1,2-diaminoethane, pyridine, pyrazine, pyrimidine, and mixtures thereof. Preferred amines include trimethylamine, triethylamine, tri-n-propylamine, tri-iso-propylamine, and tri-n-butylamine. More preferably, the tertiary amine is triethylamine or tri-n-propylamine. It will be appreciated by those skilled in the art that more than one tertiary amine may be used in the present invention. Such tertiary amines are generally commercially available from a variety of sources. Such tertiary amines may be used as is or, preferably further purified prior to use.

Halogermanes containing one or more germanium-hydrogen bonds can be prepared by a variety of methods known in the literature. For example, elemental germanium can be reacted with a gaseous mineral acid, such as gaseous hydrogen chloride, to produce halogermanes. See Equation 6.

$$Ge^0 + 2HCl\ (g) \rightarrow H_2GeCl_2 \quad (6)$$

Alternatively, germane $(GeH_4)$ may be reacted with a tetrahalogermane, typically in the presence of a catalyst such as $AlCl_3$, to produce halogermanes. The particular halogermane obtained will depend upon the stoichiometry of the starting materials.

In each of the above described reactions, the mole ratio of reagent to the germanium compound depends upon the number of reactive groups in the germanium compound that are to be exchanged. Typically, the mole ratio of any of the above reagents to the reactive group is from 1:1 to 1.3:1. Accordingly, if two reactive groups in the germanium compound are to be exchanged, the mole ratio of reagent to germanium compound is from 2:1 to 2.6:1, which corresponds to a mole ratio of reagent to reactive group of 1:1 to 1.3:1. Other amounts and ratios may be used depending upon the specific reaction conditions employed.

It will be appreciated by those skilled in the art that the order of the above reactions may be performed in any order. Typically, any step of reducing a germanium-halide compound to form a germanium-hydrogen compound will be performed last, although other orders of reaction may be advantageous.

Any of the above described methods of preparing the desired halogermanium precursor compounds may be performed in a batch, semi-batch, continuous or semi-continuous mode. For example, the present invention provides a batch as well as semi-continuous process for the preparation of halogermanium compounds, including the steps of delivering a germanium compound and alkylating agent independently to a reaction zone maintained at a predetermined temperature sufficient to allow the alkylation to proceed and the product is then separated once the reaction is complete. The halogermanium product is collected at the outlet preferably located at the top of the reactor while the byproduct in non-vaporized state is removed as waste from the reactor at the end of the reaction. The addition of reagents in a multi-step alkylation may be either in a simultaneous or sequential manner. The rate of addition of the various reagents may be controlled by using appropriate flow controllers that are known in the art.

An advantage of the present invention is that the two or more germanium compounds are substantially free of metallic impurities such as zinc and aluminum, and preferably free of zinc and aluminum. In particular, such germanium compounds are substantially free of zinc, aluminum and silicon, and preferably free of such impurities. By "substantially free" it is meant that the compounds contain less than 0.5 ppm of such impurities, and preferably less than 0.25 ppm. In another embodiment, the present germanium compounds have "5-nines" purity, i.e. a purity of $\geq 99.999\%$. More typically, the germanium compounds have a purity of "6-nines", i.e. $\geq 99.9999\%$.

The present two or more germanium compounds, particularly two or more halogermanium compounds, are suitable for use as precursors for the vapor phase deposition of germanium-containing epitaxial films, such as by LPE, ME, CBE, ALD and are particularly suitable for use as precursors in CVD. More particularly, the germanium compounds are suitable for use as precursors in the vapor phase deposition of silicon-germanium ("SiGe") films. Such films are useful in the manufacture of electronic devices, such as integrated circuits, and optoelectronic devices, and particularly in the manufacture of heterojunction bipolar transistors.

Suitable germanium compounds may be solids, liquids or gasses. When the germanium compounds are solids, liquids or gases, they may be combined into a single delivery device, such as a bubbler. For example, two or more gases, two or more liquids, two or more solids, or a combination of liquid and solid germanium compounds may be combined into a single delivery device. Alternatively, multiple delivery devices may be used. For example, a first germanium compound may be added to a first delivery device and a second germanium compound may be added to a second delivery device. It will be appreciated by those skilled in the art that either the first delivery device, the second delivery device or both delivery devices contain more than one germanium compound. It will be further appreciated that more than two delivery devices may be used. When one or more gaseous germanium compounds, such as germane, are to be used with one or more solid or liquid germanium compounds, such as germanium tetrachloride, it is preferred that the gaseous germanium compounds are not in the same delivery device as the solid and liquid germanium compounds.

In one embodiment, films including germanium are typically deposited by first placing the desired two or more halogermanium precursor compounds, i.e. source compounds, in a vapor delivery device having an outlet connected to a deposition chamber. A wide variety of vapor delivery devices may be used, depending upon the particular deposition apparatus used. When the precursor compound mixture is a solid, the devices disclosed in U.S. Pat. No. 6,444,038 (Rangarajan et al.) U.S. Pat. No. and 6,607,785 (Timmons et al.), as well as other designs, may be used. For liquid precursor compound mixtures, the devices disclosed in U.S. Pat. No. 4,506,815 (Melas et al) and U.S. Pat. No. 5,755,885 (Mikoshiba et al) may be used, as well as other liquid precursor vapor delivery devices. The source compound mixture is maintained in the vapor delivery device as a liquid or solid. Solid source compounds are typically vaporized or sublimed prior to transportation to the deposition chamber.

In another embodiment, a first halogermanium compound may be placed in a first vapor delivery device and a second germanium compound, such as a second halogermanium compound, may be placed in a second vapor delivery device. Each vapor delivery device is then connected to the same deposition apparatus. Each of the germanium compounds is then conveyed from its respective delivery device into the deposition chamber to provide two germanium compounds in the vapor phase. It will be appreciated that more than two vapor delivery devices containing germanium compounds may be used in order to provide more than two germanium compounds in the vapor phase. In a further embodiment, the two or more germanium compounds are placed in a single delivery device.

In a still further embodiment, a first germanium compound, such as germane, is placed in a first vapor delivery device and a second germanium compound, particularly a halogermanium compound such as germanium tetrachloride, germanium tetrabromide and combinations thereof, are placed in a second vapor delivery device. Both the germanium compound and the halogermanium compound are delivered to a deposition chamber in the vapor phase. Such germanium compound and halogermanium compound, in one embodiment, may react in the vapor phase to form a single compound germanium source. In this way, a stable concentration of germanium source in the vapor phase is provided.

Accordingly, the present invention provides a vapor delivery device for feeding a fluid stream saturated with a germanium compound suitable for depositing a film containing germanium to a chemical vapor deposition system including a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing two or more germanium compounds as described above; the inlet opening being in fluid communication with the chamber and the chamber being in fluid communication with the outlet opening.

In another embodiment, the present invention provides an apparatus for chemical vapor deposition of metal films including one or more of the vapor delivery devices for feeding a fluid stream saturated with two or more germanium compounds described above. Such vapor delivery devices may be used to provide the germanium compounds in the vapor phase to a single deposition chamber or to a plurality of deposition chambers.

The source compounds are typically transported to the deposition chamber by passing a carrier gas through the vapor delivery device. Suitable carrier gasses include nitrogen, hydrogen, and mixtures thereof. In general, the carrier gas is introduced below the surface of the source compounds, and bubbles up through the source compounds to the headspace above it, entraining or carrying vapor of the source compounds in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The deposition chamber temperature is from 200° to 1200° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, sapphire, and the like. Such substrates are particularly useful in the manufacture of integrated circuits.

Deposition is continued for as long as desired to produce a film including germanium having the desired properties. Typically, the film thickness will be from several tens of nanometers to several hundreds of microns.

The present invention further provides a method for manufacturing an electronic device including the step of depositing a film including germanium on an electronic device substrate including the steps of: a) conveying two or more germanium compounds in a gaseous phase to a deposition chamber containing the substrate, wherein a first germanium compound is a halogermanium compound of the formula $X^1_{4-a}GeR_a$, wherein $a=0-3$, each $X^1$ is independently a halogen, and each R is independently chosen from H, alkyl, alkenyl, alkynyl, aryl, and $NR^3R^4$, wherein each $R^3$ and $R^4$ are independently chosen from H, alkyl, alkenyl, alkynyl and aryl, and wherein a second germanium compound has the formula

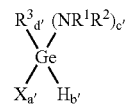

wherein each $R^1$ and $R^2$ are independently chosen from H, alkyl, alkenyl, alkynyl and aryl; each $R^3$ is independently chosen from alkyl, alkenyl, alkynyl and aryl; X is halogen; $a'=0-4$; $b'=0-4$; $c'=0-3$; $d'=0-4$ and $a'+b'+c'+d'=4$; provided that $a'+b'\leq 3$ when $X^1=Cl$, $R=H$, and $X=Cl$; b) decomposing the two or more germanium compounds in the deposition chamber; and c) depositing the film comprising germanium on the substrate.

The present invention is particularly suitable for the deposition of germanium-containing films, such as SiGe films. SiGe films are being employed for two technologies. One well-established major application is Bipolar CMOS or BiCMOS where a thin (40 to 80 nm) SiGe film is used as the base of a high frequency HBT. The substrate for the deposition of this SiGe base film and the subsequent Si collector film is a highly structured silicon wafer with the CMOS circuitry mostly finished. The other application for SiGe CVD is the area of strained silicon or s-Si. Here a deposition of a thick 3 to 5 micrometer SiGe layer takes place on a plain silicon wafer. Subsequent to the growth of the SiGe film a thin (20 nm) Si film is grown. This silicon film adopts the crystal lattice of the underlying SiGe layer (strained silicon). Strained silicon shows much faster electrical responses than regular silicon.

In another embodiment, a method for fabricating a device containing a group of silicon-germanium layers is illustrated by the steps of: i) providing a substrate including a surface layer of a group IV element, ii) maintaining the substrate at a temperature ranging from 400° C. to 600° C., iii) forming a layer of $Si_{1-x}Ge_x$, where x ranges from 0 to 0.50, on the substrate by MOCVD using two or more of the above-described germanium compounds; iv) maintaining the substrate at about the temperature of step i) and continuing a silicon precursor flow with a flow of the germanium compounds completely switched off, in order to obtain abrupt interfaces, and v) maintaining the substrate at about the temperature of step i), and forming a cap layer of strained silicon, thereby improving the mobility of electrons and speed of the device.

The following examples are expected to illustrate further various aspects of the present invention, but are not intended to limit the scope of the invention in any aspect. All manipulations are performed in an inert atmosphere, typically under an atmosphere of dry nitrogen.

EXAMPLE 1

Dimethylamino germanium trichloride is expected to be synthesized according to the equation:

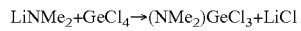

$LiNMe_2 + GeCl_4 \rightarrow (NMe_2)GeCl_3 + LiCl$

To a stirred solution of germanium tetrachloride (50 g, 0.233 moles) in pentane (100 mL) maintained at 0° C., is added dropwise a solution of lithium dimethylamide in diethyl ether (11.898 g, 0.233 moles, 50 mL) via pressure equalized addition funnel. The addition lasts for approximately 30 minutes. When the addition is completed, the resulting mixture is allowed to slowly warm to room temperature after which a suspension is expected to be obtained.

When the suspension settles, the supernatant mother liquor is separated using a siphon technique. The precipitate of lithium chloride byproduct is washed with fresh pentane and the washings are separated via siphon under nitrogen atmosphere, and are subsequently combined with the mother liquor. The pentane/ether solvents are then removed via atmospheric pressure distillation by heating the reaction mass to 60° C. The expected crude product obtained may be further purified by vacuum distillation and is expected to yield high purity (dimethylamino) germanium trichloride free of metallic impurities and organic solvents.

EXAMPLE 2

To a conventional vapor delivery device are added (dimethylamino) germanium trichloride and germanium tetrachloride in an expected molar ratio of 45:55.

EXAMPLE 3

The procedure of Example 2 is repeated except that the germanium compounds in the table are expected to be used in the molar ratios shown. The molar ratios reported are the expected moles of halogermanium compound: second germanium compound.

| Sample | Halogermanium Compound | Second Germanium Compound | Molar Ratio |
| --- | --- | --- | --- |
| A | GeCl$_4$ | Me$_4$Ge | 95:5 |
| B | GeCl$_4$ | t-Bu(Me)GeH$_2$ | 70:30 |
| C | GeCl$_4$ | i-PrGeMe$_3$ | 25:75 |
| D | GeBr$_4$ | Me$_4$Ge | 80:20 |
| E | GeBr$_4$ | (H$_2$C=CH)GeMe$_3$ | 40:60 |
| F | GeBr$_4$ | t-BuGeH$_3$ | 5:95 |
| G | GeI$_4$ | Et$_2$GeCl$_2$ | 70:30 |
| H | GeI$_4$ | (NMe$_2$)GeCl$_3$ | 45:55 |
| I | GeI$_4$ | (NMe$_2$)GeCl$_3$ | 20:80 |
| J | Me$_3$GeCl | t-Bu(Me)GeH$_2$ | 95:5 |
| K | Me$_3$GeCl | t-Bu(Me)GeH$_2$ | 22:78 |
| L | Me$_3$GeCl | i-PrGe Me$_3$ | 65:35 |
| M | MeGeCl$_3$ | Et$_4$Ge | 90:10 |
| N | MeGeCl$_3$ | (H$_2$C=CH)GeMe$_3$ | 35:65 |
| O | MeGeCl$_3$ | i-PrGeMe$_3$ | 10:90 |
| P | t-BuGeCl$_3$ | (NMe$_2$)GeCl$_3$ | 50:50 |
| Q | t-BuGeCl$_3$ | Me(NMe$_2$)GeCl$_2$ | 38:62 |
| R | t-BuGeCl$_3$ | t-BuGeH$_3$ | 25:75 |
| S | H$_2$GeCl$_2$ | Me$_2$(i-Pr)GeH | 57:43 |
| T | GeCl$_4$ | GeBr$_4$ | 22:78 |
| U | GeBr$_4$ | HGeCl$_3$ | 42:58 |
| V | Et$_2$GeBr$_2$ | t-Bu(NMe$_2$)GeCl$_2$ | 30:70 |
| W | Me$_2$GeHCl | i-Pr(Me)GeH$_2$ | 47:53 |
| X | MeGeHCl$_2$ | Me(Et)GeH$_2$ | 21:79 |
| Y | MeGeF$_3$ | Me$_2$GeEt$_2$ | 34:66 |
| Z | Me$_2$GeF$_2$ | Et$_2$(Me)GeH | 15:85 |
| AA | i-BuGeCl$_3$ | i-BuGeH$_3$ | 50:50 |
| BB | n-PrGeCl$_3$ | n-PrGeH$_3$ | 42:58 |

In the above table, the following abbreviations are used: Me=methyl, Et=ethyl, i-Pr=iso-propyl n-Pr-n-propyl, i-Bu-iso-butyl and t-Bu=tert-butyl.

EXAMPLE 4

A germanium film is expected to be grown on a sapphire substrate using the delivery device of Example 3 containing Sample B attached to a MOCVD apparatus. The delivery device is heated and a carrier gas (H$_2$ and/or N$_2$) is passed through the heated delivery device. The carrier gas saturated with vapor phase germanium compounds is directed to a deposition chamber containing the sapphire substrate. The deposition chamber is maintained at a temperature sufficient to induce decomposition of the vapor phase germanium compounds. A germanium film is expected to be deposited on the sapphire substrate. Deposition is expected to be continued until a desired thickness of the germanium film is achieved.

EXAMPLE 5

The procedure of Example 4 is repeated except that two delivery devices are expected to be used. The first delivery device is expected to contain tetrachlorogermane and the second delivery device is expected to contain germane (GeH$_4$).

EXAMPLE 6

The procedure of Example 4 is repeated except that two delivery devices are expected to be used, a first delivery device expected to contain germanium tetrachloride and a second delivery device expected to contain tert-butyl methyl germane.

EXAMPLE 7

A group of Si$_x$Ge$_{1-x}$ epitaxial structures are expected to be grown by MOCVD on (0001) sapphire substrates. A first delivery device containing disilane is attached to a MOCVD apparatus. A second delivery device from Example 2 is attached to the MOCVD apparatus. The delivery devices are heated and a carrier gas (H$_2$ and/or N$_2$) is passed through each heated delivery device. The carrier gas saturated with vapor phase disilane and the carrier gas saturated with vapor phase germanium compounds are directed to a deposition chamber containing the sapphire substrate. The deposition chamber is maintained at a temperature sufficient to induce decomposition of the vapor phase compounds (e.g. 650° C. and 750° C.). For this group of layers, a 1 to 2 µm thick Si$_{0.9}$Ge$_{0.1}$ layer is expected to be first grown on a silicon substrate. Subsequent layers of composition Si$_{0.8}$Ge$_{0.2}$, Si$_{0.7}$Ge$_{0.3}$, and Si$_{0.6}$Ge$_{0.4}$ are expected to be grown by increasing the mass flow rate of the germanium precursors. After deposition of the Si$_{1-x}$Ge$_x$ graded layers, the silicon precursor flow is continued with the germanium precursor flow completely switched off, in order to obtain abrupt interfaces. Silicon deposition is expected to be carried out using the graded SiGe as the underlying layer, and epitaxial strained silicon layer is deposited as the cap layer.

What is claimed is:

1. A method of depositing a film containing germanium on a substrate comprising the steps of:
   a) conveying two or more germanium compounds in a gaseous phase to a deposition chamber containing the substrate, wherein a first germanium compound is a halogermanium compound of the formula X$^1_{4-a}$GeR$_a$, wherein a=0–3, each X$^1$ is independently a halogen, and each R is independently chosen from H, alkyl, alkenyl, alkynyl, aryl, and NR$^4$R$^6$, wherein each R$^4$ and R$^6$ are independently chosen from H, alkyl, alkenyl, alkynyl and aryl, and wherein a second germanium compound has the formula

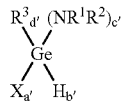

wherein each R$^1$ and R$^2$ are independently chosen from H, alkyl, alkenyl, alkynyl and aryl; each R$^3$ is independently chosen from alkyl, alkenyl, alkynyl and aryl; X is halogen; a'=0–3; b'=0–3; c'=0–3; d'=1–4 and a'+b'+c'+d'=4; provided that a'+b'≦3 when X$^1$=Cl, R=H, and X=Cl;
   b) decomposing the two or more germanium compounds in the deposition chamber; and
   c) depositing the film comprising germanium on the substrate.

2. The method of claim 1 wherein the two or more germanium compounds are provided from a single vapor delivery device.

3. The method of claim 1 wherein the first germanium compound is provided from a first vapor delivery device and the second germanium compound is provided from a second vapor delivery device.

4. The method of claim 3 wherein the first germanium compound is chosen from germanium tetrachloride and germanium tetrabromide.

5. The method of claim 1 wherein c'=1–3.

6. The method of claim 1 wherein a'=c'=0, b'=1–2 and d'=2–3.

7. A method of depositing a film containing germanium on a substrate comprising the steps of:
   a) conveying two or more germanium compounds in a gaseous phase to a deposition chamber containing the substrate, wherein a first germanium compound is a halogermanium compound of the formula X$^1_{4-a}$GeR$_a$, wherein a=0–3, each X$^1$ is independently a halogen, and each R is independently chosen from H, alkyl, alkenyl, alkynyl, aryl, and NR$^4$R$^6$, wherein each R$^4$ and R$^6$ are independently chosen from H, alkyl, alkenyl, alkynyl and aryl, provided that the first germanium compound is chosen from GeCl$_4$, GeBr$_4$ and GeI$_4$ when a=0 and each X$^1$ is the same; and wherein a second germanium compound has the formula

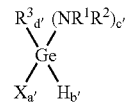

wherein each R$^1$ and R$^2$ are independently chosen from H, alkyl, alkenyl, alkynyl and aryl; each R$^3$ is independently chosen from alkyl, alkenyl, alkynyl and aryl; X is halogen; a'=0–4; b'=0–4; c'=0–3; d'=0–4 and a'+b'+c'+d'=4; provided that a'+b'≦3 when X$^1$=Cl, R=H, and X=Cl;
   b) decomposing the two or more germanium compounds in the deposition chamber; and
   c) depositing the film comprising germanium on the substrate.

8. The method of claim 7 wherein d'=1–4.

9. The method of claim 7 wherein a=1–3.

10. The method of claim 7 wherein the first germanium compound is chosen from tetrachloro germane, tetrabromo germane, tetraiodo germane, chloro tribromo germane, dichloro dibromo germane, trichloro bromo germane, trichloro iodo germane, dichloro diiodo germane, trichloro iodo germane, tribromo iodo germane, dibromo diiodo germane, bromo triiodo germane, dichloro bromo iodo germane, chloro dibromo iodo germane, chloro bromo diiodo germane, trichloro fluoro germane, dichloro difluoro germane, chloro trifluoro germane, tribromo fluoro germane, dibromo difluoro germane, bromo trifluoro germane, iodo trifluoro germane, diiodo difluoro germane, triiodo fluoro germane, chloro bromo iodo fluoro germane, dichloro bromo fluoro germane, chloro dibromo fluoro germane, dibromo iodo fluoro germane, bromo diiodo fluoro germane, dichloro iodo fluoro germane and chloro diiodo fluoro germane; and iso-propyl (dimethylamino) germanium dichloride; methyl (dimethylamino) germanium dichloride; methyl (dimethylamino) germanium dibromide; dichloro (diethylamino) germane; dichloro ethyl (diethylamino) germane; dichloro tert-butyl (diethylamino) germane; dichloro bis(dimethylamino) germane; and chloro ethyl (dimethylaminopropyl) (dimethylamino) germane; dichloro tert-butyl (dimethylamino) germane; chloro di-iso-propyl (dimethylamino) germane; trimethyl germanium chloride; methyl germanium trichloride; trimethyl germanium fluoride; trimethyl germanium bromide; tris(trifluoromethyl) germanium iodide; methyl germanium trifluoride; dimethyl germanium difluoride; dichloro methyl germane; dimethyl germanium dichloride; trimethyl germanium iodide; vinyl germanium trichloride; ethyl germanium trichloride; chloro tert-butyl dimethyl germane; allyl germanium trichloride; tert-butyl germanium trichloride; diethyl germanium dichloride; trimethyl germanium chloride; n-butyl germanium trichloride; trimethyl germanium bromide; di-n-butyl germanium dichloride; phenyl germanium dichloride; tri-n-butyl germanium bromide; tri-n-butyl germanium chloride; and benzyl germanium trichloride.

11. A method of depositing a film containing germanium on a substrate comprising the steps of:
   a) conveying two or more germanium compounds in a gaseous phase to a deposition chamber containing the substrate, wherein a first germanium compound is a halogermanium compound of the formula $X^1_{4-a}GeR_a$, wherein $a=0-3$, each $X^1$ is independently a halogen, and each R is independently chosen from H, alkyl, alkenyl, alkynyl, aryl, and $NR^4R^6$, wherein each $R^4$ and $R^6$ are independently chosen from H, alkyl, alkenyl, alkynyl and aryl, and wherein a second germanium compound has the formula

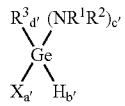

wherein each $R^1$ and $R^2$ are independently chosen from H, alkyl, alkenyl, alkynyl and aryl; each $R^3$ is independently chosen from alkyl, alkenyl, alkynyl and aryl; X is halogen; $a'=0-4$; $b'=0-4$; $c'=0-3$; $d'=0-4$ and $a'+b'+c'+d'=4$; wherein at least one of $a'$, $c'$ and $d'$ is not 0; provided that $a'+b'\leq 3$ when $X^1=Cl$, R=H, and X=Cl;
   b) decomposing the two or more germanium compounds in the deposition chamber; and
   c) depositing the film comprising germanium on the substrate.

12. The method of claim 11 wherein the second germanium compound is chosen from alkyl germanes, amino germanes and halogermanium compounds.

13. The method of claim 12 wherein the second germanium compound is chosen from tetramethyl germane, tetraethyl germane, tetra-n-propyl germane, methyl germane, dimethyl germane, trimethyl germane, ethyl germane, diethyl germane, trimethyl germane, dimethyl diethyl germane, tert-butyl methyl germane, tert-butyl dimethyl germane, tert-butyl trimethyl germane, tert-butyl ethyl germane, tert-butyl diethyl germane, tert-butyl trimethyl germane, tert-butyl iso-propyl germane, methyl tert-butyl iso-propyl germane, iso-propyl germane, di-iso-propyl germane, di-iso-propyl dimethyl germane, tri-iso-propyl germane, tri-iso-propyl methyl germane, di-iso-propyl diethyl germane, (dimethylamino) germane, bis-(dimethylamino) germane, methyl (dimethylamino) germane, ethyl (dimethylamino) germane, diethyl (diethylamino) germane, tert-butyl (dimethylamino)germane, tert-butyl bis(dimethylamino) germane, ethyl tert-butyl bis(dimethylamino) germane, iso-propyl (dimethylamino)germane, iso-propyl (diethylamino) germane, di-iso-propyl bis(dimethylamino) germane, n-propyl (dimethylamino) germane, n-propyl (diethylamino) germane; tert-butyl dimethyl germanium chloride, tert-butyl dimethyl germanium bromide, tert-butyl diethyl germanium chloride, tert-butyl diethyl germanium iodide, dimethyl germanium dichloride, trimethyl germanium chloride, trimethyl germanium bromide, tert-butyl germanium trichloride, iso-propyl germanium chloride, iso-propyl germanium trichloride, di-iso-propyl germanium dibromide, iso-propyl dimethyl germanium chloride, iso-propyl methyl germanium dichloride, and iso-propyl dimethyl germanium bromide.

14. The method of claim 11 wherein the two or more germanium compounds are present in a mole ratio of 5:95 to 95:5.

15. The method of claim 14 wherein the two or more germanium compounds are present in a mole ratio of 25:75 to 75:25.

* * * * *